(12) United States Patent
Watanabe et al.

(10) Patent No.: US 9,767,252 B2
(45) Date of Patent: Sep. 19, 2017

(54) COMPUTER PRODUCT, RENDERING METHOD, AND RENDERING APPARATUS

(71) Applicants: FUJITSU LIMITED, Kawasaki-shi, Kanagawa (JP); The University of Tokyo, Tokyo (JP)

(72) Inventors: Masahiro Watanabe, Kawasaki (JP); Yoshimasa Kadooka, Kawasaki (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: FUJITSU LIMITED, Kawasaki (JP); THE UNIVERSITY OF TOKYO, Tokyo (JP)

(*) Notice: Subject to any disclaimer, the term of this patent is extended or adjusted under 35 U.S.C. 154(b) by 204 days.

(21) Appl. No.: 13/911,578

(22) Filed: Jun. 6, 2013

(65) Prior Publication Data

US 2013/0328868 A1   Dec. 12, 2013

(30) Foreign Application Priority Data

Jun. 8, 2012   (JP) ................................ 2012-131243

(51) Int. Cl.
  *G06T 15/00* (2011.01)
  *G06F 19/00* (2011.01)
  (Continued)

(52) U.S. Cl.
  CPC ........ *G06F 19/321* (2013.01); *G06F 17/5009* (2013.01); *G06T 19/00* (2013.01); *G06T 2219/008* (2013.01)

(58) Field of Classification Search
  None
  See application file for complete search history.

(56) References Cited

U.S. PATENT DOCUMENTS 5,889,524 A      3/1999   Sheehan et al.
6,301,496 B1 *  10/2001   Reisfeld ........................ 600/407
                          (Continued)

FOREIGN PATENT DOCUMENTS

JP      2003-141566      5/2003
JP      2006-154965      6/2006
                  (Continued)

OTHER PUBLICATIONS

"ParaView User's Guide (Version 1.6,)" Kitware, Inc., Sep. 1, 2004, pp. 1-69 and 70-71.

(Continued)

*Primary Examiner* — Andrew G Yang
(74) *Attorney, Agent, or Firm* — Staas & Halsey LLP

(57) ABSTRACT

A computer-readable recording medium stores a rendering program that causes a computer to execute process that includes acquiring an internal organ model that is a set of elements having physical values according each position of an internal organ; setting a plurality of planes that form given angles with a line of sight from a viewpoint position, and intersect the internal organ model; assigning among the set of elements, a physical value of an element intersected by a plane set at the setting, to an element cross section that is a plane where the plane set at the setting intersects the element; and rendering, based on the physical value, the element cross section to which the physical value has been assigned.

6 Claims, 13 Drawing Sheets

(51) Int. Cl.
*G06T 19/00* (2011.01)
*G06F 17/50* (2006.01)

(56) References Cited

U.S. PATENT DOCUMENTS

| | | | |
|---|---|---|---|
| 2003/0169911 A1* | 9/2003 | Snyder | G06T 5/50 382/130 |
| 2004/0210307 A1* | 10/2004 | Khairkhahan | 623/2.18 |
| 2006/0034513 A1* | 2/2006 | Cai et al. | 382/173 |
| 2007/0014452 A1 | 1/2007 | Suresh et al. | |
| 2007/0070068 A1* | 3/2007 | John | G06T 19/00 345/424 |
| 2008/0262814 A1* | 10/2008 | Zheng | G06F 19/3437 703/11 |
| 2008/0319308 A1 | 12/2008 | Tang | |
| 2010/0204589 A1* | 8/2010 | Swoboda | A61B 5/02007 600/485 |
| 2010/0318326 A1* | 12/2010 | Yamamoto | G06F 17/5018 703/1 |
| 2011/0150312 A1* | 6/2011 | Takanami et al. | 382/131 |
| 2012/0041318 A1 | 2/2012 | Taylor | |
| 2012/0155723 A1* | 6/2012 | Deno | G06T 7/0044 382/128 |

FOREIGN PATENT DOCUMENTS

| | | |
|---|---|---|
| WO | 2006/067719 A2 | 6/2006 |
| WO | 2010/034117 A1 | 4/2010 |

OTHER PUBLICATIONS

Inoue, Yusuke, et al., "Development of surgical simulator with high-quality visualization based on finite-element method and deformable volume rendering", Journal of the Institute of Electronics, Information and Communication Engineers, Japan, the Institute of Electronics, Information and Communication Engineers, Jan. 1, 2004, vol. J87-D-II, No. 1, pp. 271-280.

Office Action of Japan Patent Application 2012-131243 dated Nov. 10, 2015.

Extended European Search Report mailed Apr. 4, 2017 in related European Application No. 13170627.7.

Megumi Nakao et al., "Evaluation and User Study of Haptic Simulator for Learning Palpation in Cardiovascular Surgery", XP003006000, International Conference on Artificial Reality and Tele-Existence, Dec. 3, 2003, pp. 203-208.

Michael A. Guttman et al., "Analysis of Cardiac Function from MR Images", IEEE Computer Graphics and Applications, IEEE Service Center, New York, NY, US, vol. 17, No. 1, Jan. 1, 1997, pp. 30-38.

* cited by examiner

FIG.4

| ID | FIRST VERTEX | SECOND VERTEX | THIRD VERTEX | FOURTH VERTEX | CENTER OF GRAVITY | PHYSICAL VALUE | ATTRIBUTE FIELD | CROSS SECTION PASSING |
|---|---|---|---|---|---|---|---|---|
| t1 | v1(t1) | v2(t1) | v3(t1) | v4(t1) | g(t1) | e(t1) | a(t1) | 0 |
| t2 | v1(t2) | v2(t2) | v3(t2) | v4(t2) | g(t2) | e(t2) | a(t2) | 1 |
| .. | .. | .. | .. | .. | .. | .. | .. | .. |
| ti | v1(ti) | v2(ti) | v3(ti) | v4(ti) | g(ti) | e(ti) | a(ti) | 0 |
| .. | .. | .. | .. | .. | .. | .. | .. | .. |
| tn | v1(tn) | v2(tn) | v3(tn) | v4(tn) | g(tn) | e(tn) | a(tn) | 0 |

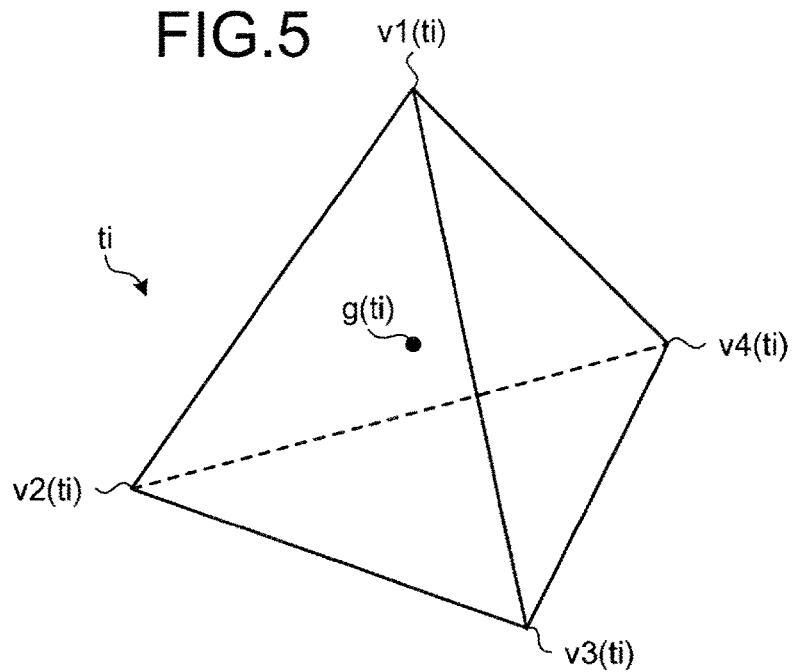

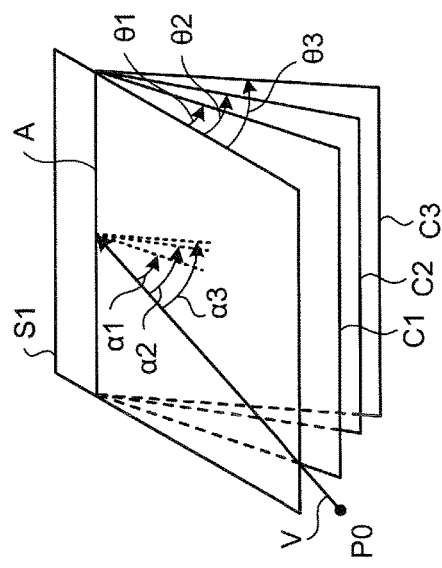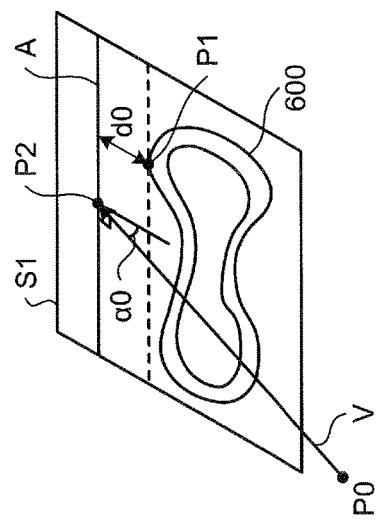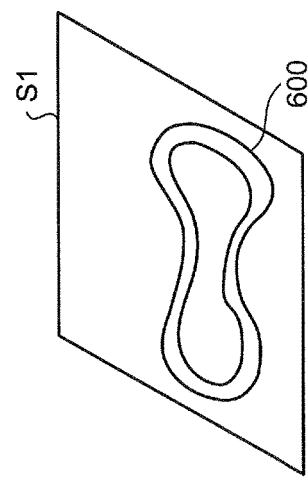

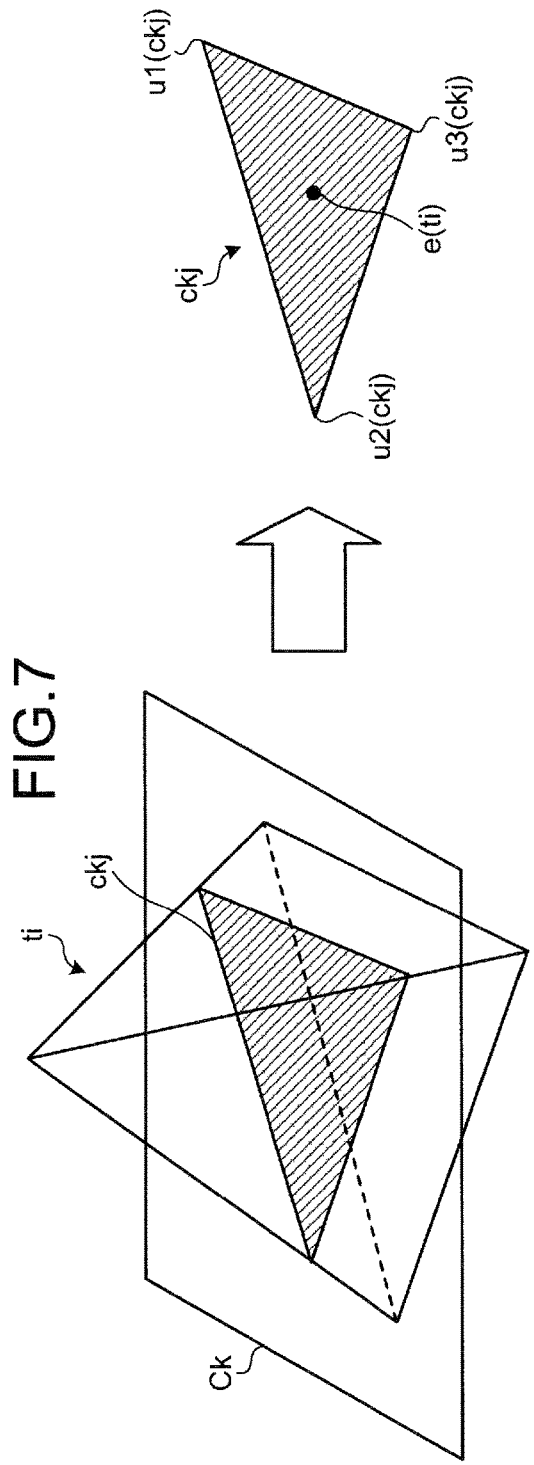

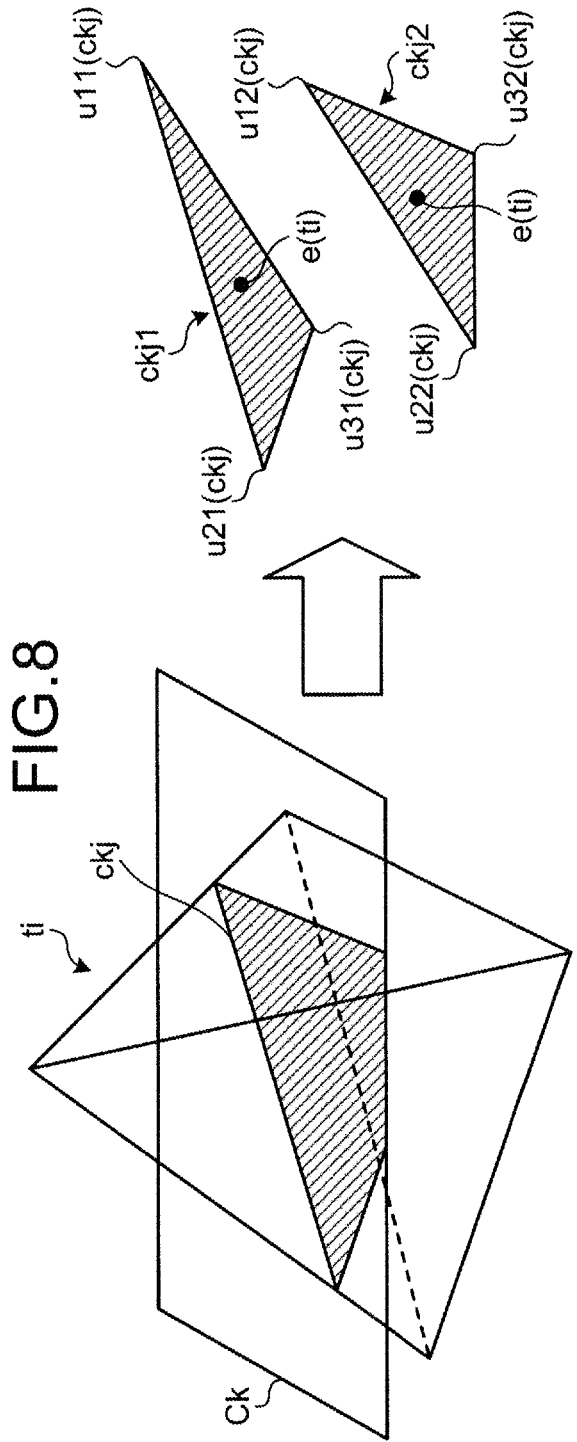

FIG.9

| ID | FIRST VERTEX | SECOND VERTEX | THIRD VERTEX | PHYSICAL VALUE |
|---|---|---|---|---|
| ck1 | u1(ck1) | u2(ck1) | u3(ck1) | e(ck1) |
| ck2 | u1(ck2) | u2(ck2) | u3(ck2) | e(ck2) |
| ⋮ | ⋮ | ⋮ | ⋮ | ⋮ |
| ckj | u1(ckj) | u2(ckj) | u3(ckj) | e(ckj) |
| ⋮ | ⋮ | ⋮ | ⋮ | ⋮ |
| ckmk | u1(ckmk) | u2(ckmk) | u3(ckmk) | e(ckmk) |

FIG.10

| PHYSICAL VALUE | R | G | B |
|---|---|---|---|
| 0 | 1.0 | 1.0 | 1.0 |
| 1 | 1.0 | 0.9 | 0.9 |
| 2 | 1.0 | 0.8 | 0.8 |
| 3 | 1.0 | 0.7 | 0.7 |
| 4 | 1.0 | 0.6 | 0.6 |
| 5 | 1.0 | 0.5 | 0.5 |
| 6 | 1.0 | 0.4 | 0.4 |
| 7 | 1.0 | 0.3 | 0.3 |
| 8 | 1.0 | 0.2 | 0.2 |
| 9 | 1.0 | 0.1 | 0.1 |
| 10 | 1.0 | 0.0 | 0.0 |

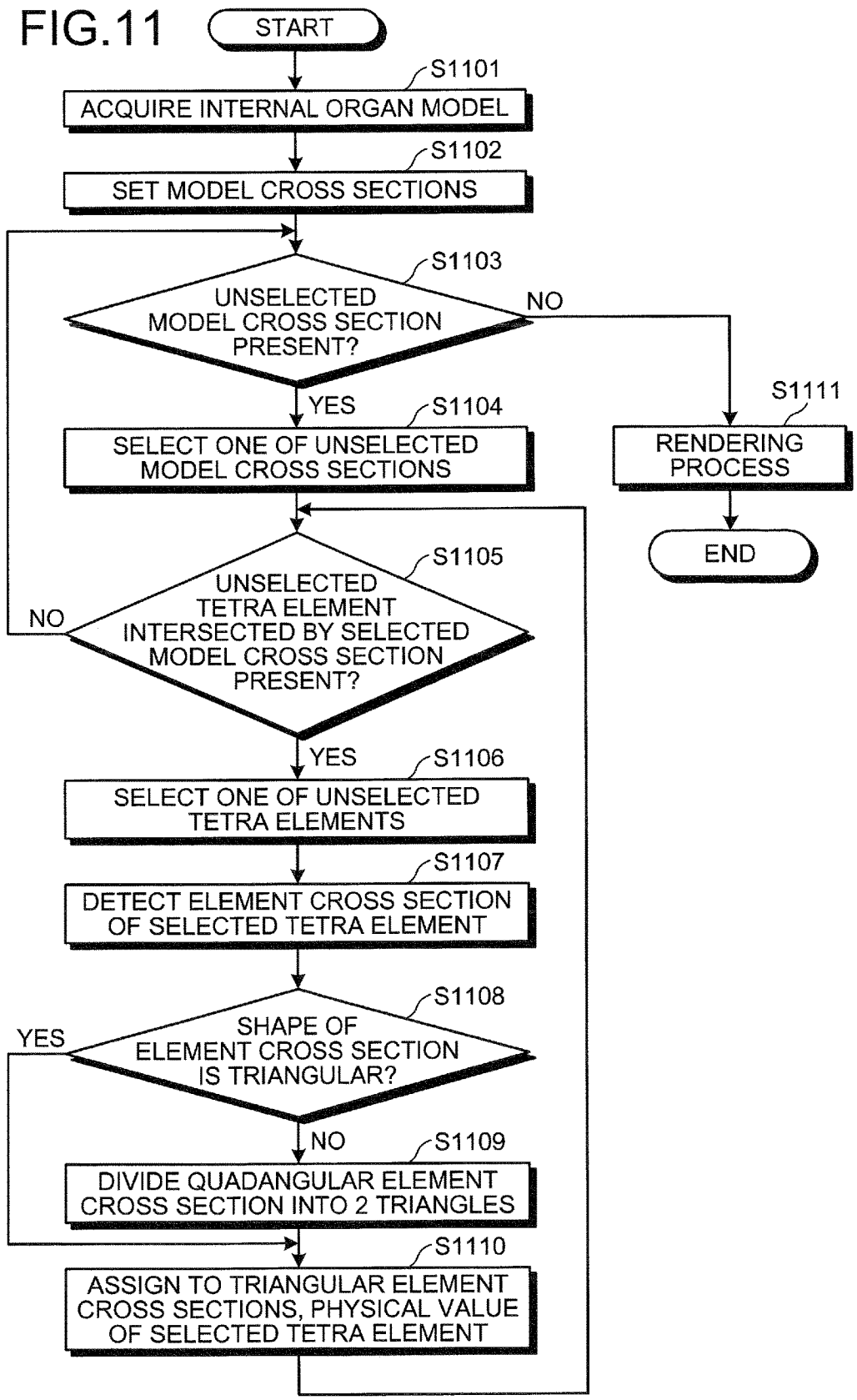

COMPUTER PRODUCT, RENDERING METHOD, AND RENDERING APPARATUS

CROSS REFERENCE TO RELATED APPLICATIONS

This application is based upon and claims the benefit of priority of the prior Japanese Patent Application No. 2012-131243, filed on Jun. 8, 2012, the entire contents of which are incorporated herein by reference.

FIELD

The embodiments discussed herein are related to a computer product, a rendering method, and a rendering apparatus.

BACKGROUND

The heart is an internal organ that pumps blood and numerical analysis is performed that reproduces this function of the heart. In the numerical analysis of the heart, a visualization technique is known in which to confirm the distribution of physical values of the interior of the heart, a cross section is virtually generated (see, for example, Kitware, Inc., "ParaView Users Guide", Sep. 1, 2004, pp. 70-71).

Nonetheless, when continuous physical values of the heart are to be viewed from a designated direction, by simply displaying multiple cross sections orthogonal to the designated direction, a problem arises in that it is difficult to intuitively discern which of the positions of cross sections corresponds. Therefore, with the conventional technology above, a problem arises in that it takes time to comprehend the gist of the intuitively difficult to understand distributions of the physical values of the interior of the heart. Such a problem is not limited to the heart and occurs with other internal organs such as the liver and kidneys.

SUMMARY

According to an aspect of an embodiment, a computer-readable recording medium stores a rendering program that causes a computer to execute process that includes acquiring an internal organ model that is a set of elements having physical values according each position of an internal organ; setting a plurality of planes that form given angles with a line of sight from a viewpoint position, and intersect the internal organ model; assigning among the set of elements, a physical value of an element intersected by a plane set at the setting, to an element cross section that is a plane where the plane set at the setting intersects the element; and rendering, based on the physical value, the element cross section to which the physical value has been assigned.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF RENDERINGS

FIG. 4 is diagram depicting an example of a data structure of the heart model according to the first embodiment;

FIG. 5 is a diagram depicting an example of tetra element ti according to the first embodiment;

Figure 12B:
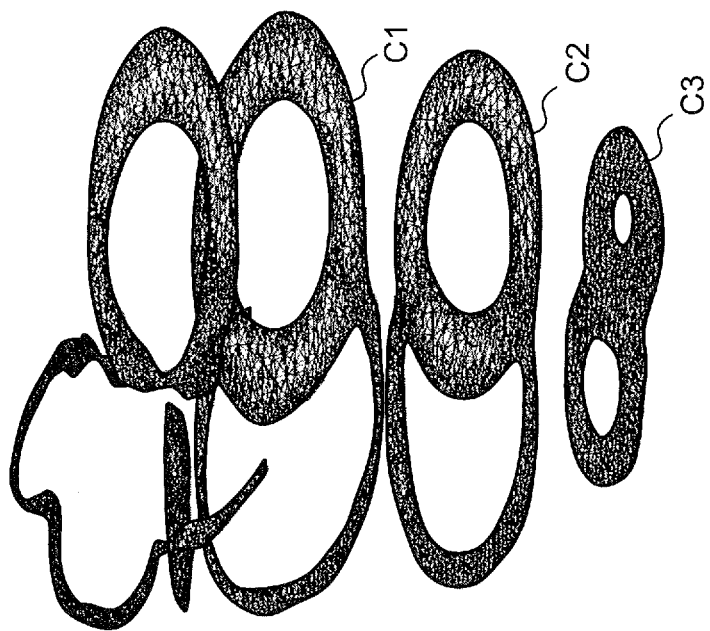
Figure 12A:
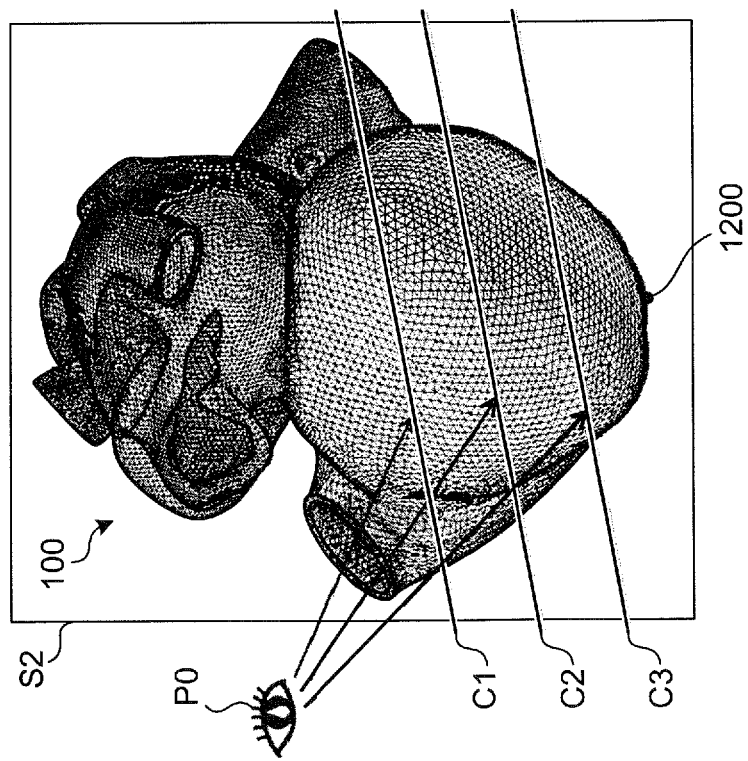
Figure 13:
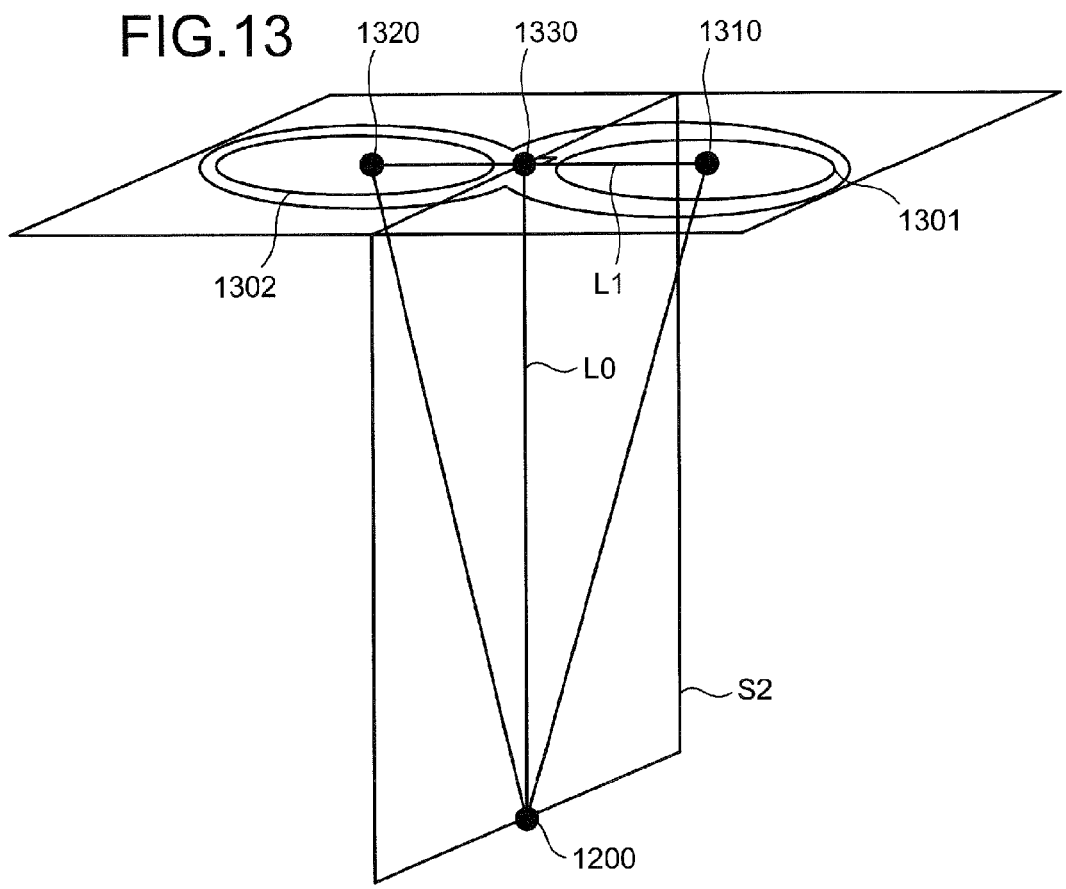
Figure 14:
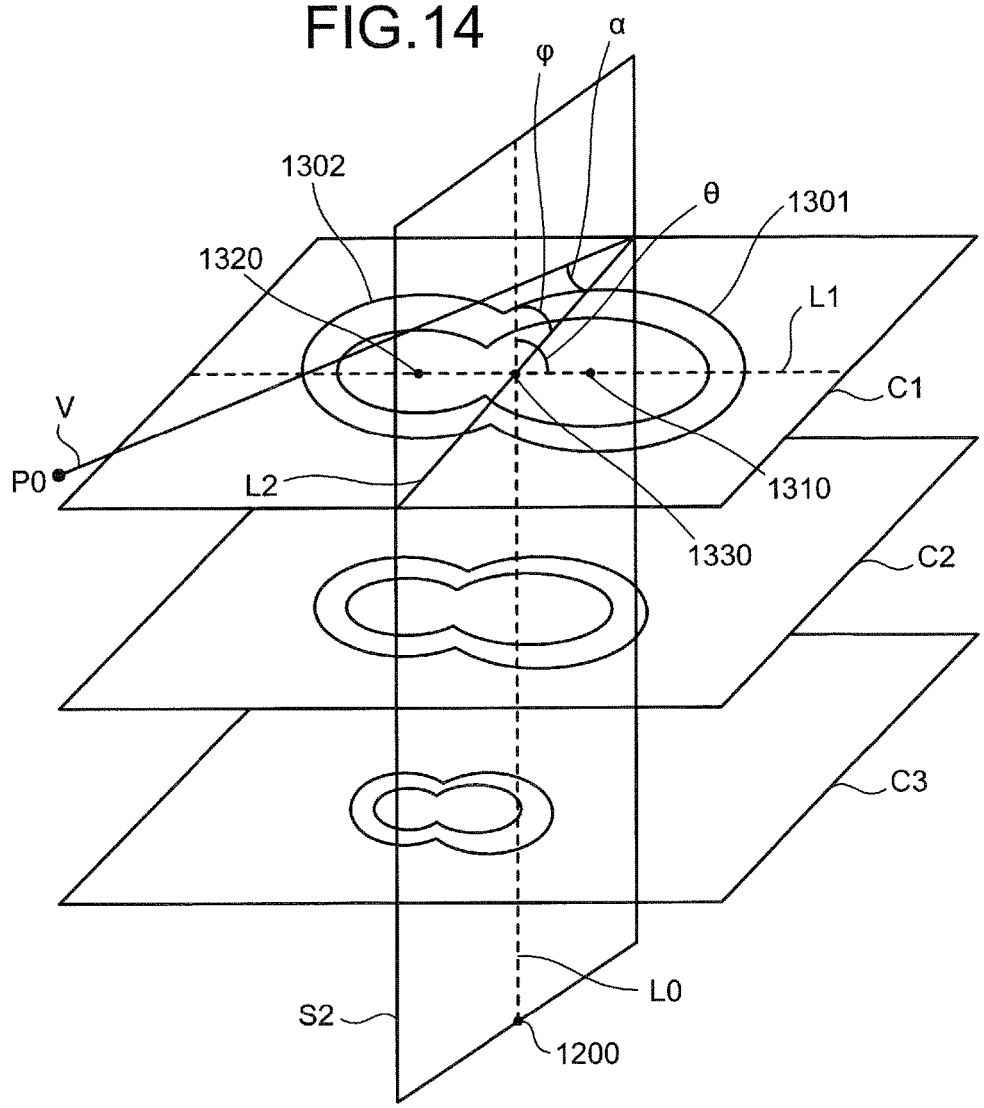

FIGS. 6A, 6B, and 6C are diagrams depicting an example of model cross section setting by a setting unit according to the first embodiment;

FIG. 7 is a diagram depicting a first example of element cross section detection according to the first embodiment;

FIG. 8 is diagram depicting a second example of element cross section detection according to the first embodiment;

FIG. 9 is a diagram depicting an example of a data structure of an element cross section according to the first embodiment;

FIG. 10 is diagram depicting an example of a color map according to the first embodiment;

FIG. 11 is a flowchart of an example of a rendering process according to the first embodiment;

FIGS. 12A and 12B are diagrams depicting a cross-section rendering example of the heart model;

FIG. 13 is diagram depicting an example of a setting method for a reference plane S1; and FIG. 14 is diagram depicting an example of a setting method for a model cross section.

DESCRIPTION OF EMBODIMENTS

Preferred embodiments of a rendering program, a rendering method, and a rendering apparatus according to the present invention will be explained in detail with reference to the accompanying renderings. In the present embodiments, although description is given using a 3-dimensional model of a heart as one example of an internal organ, implementation may be by a 3-dimensional model of another internal organ other than the heart.

Figure 1A:
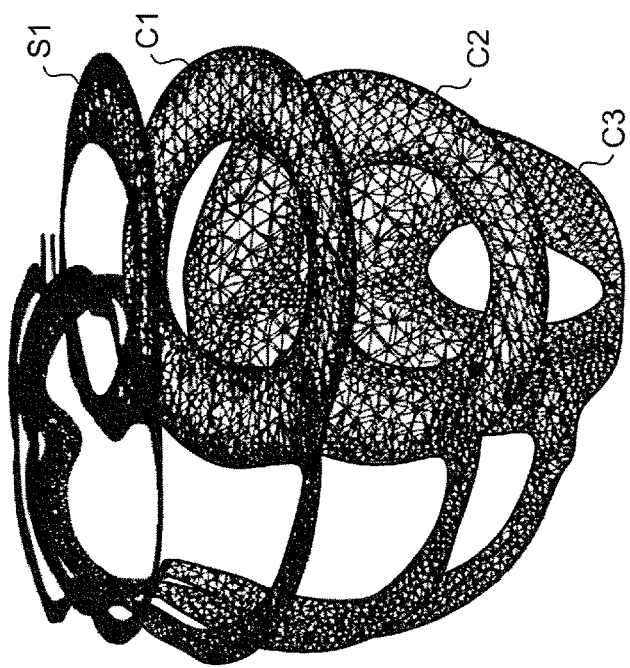
FIGS. 1A and 1B are diagrams depicting a cross-section rendering example of a heart model according to a first embodiment.
Figure 1B:
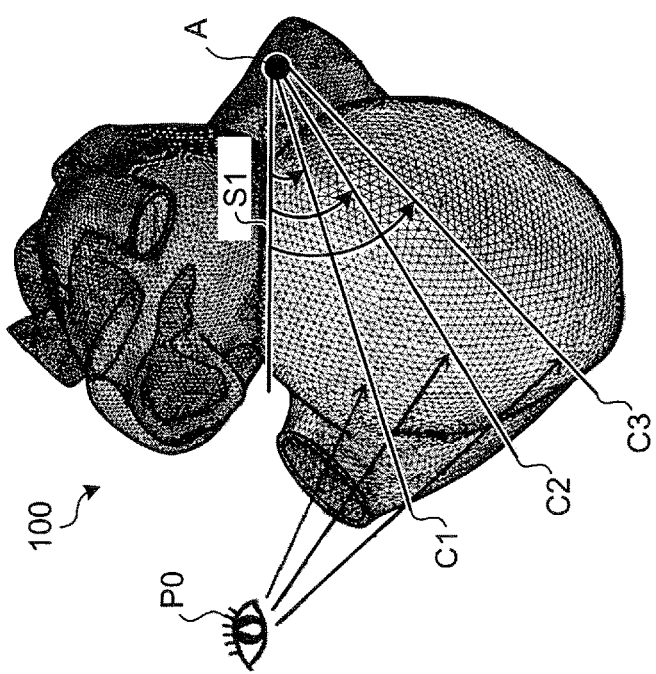

FIGS. 1A and 1B are diagrams depicting a cross-section rendering example of a heart model according to a first embodiment. FIG. 1A depicts a 3-dimensional model of a heart. Hereinafter, the 3-dimensional model of the heart is referred to as a "heart model". A heart model 100, for example, is a set of tetrahedral elements (unstructured grid data) called tetra elements. Each tetra element has a physical value corresponding to the position of the tetra element. A physical value is a value indicative of the behavior of the cardiac muscle corresponding to the tetra element; and, for example, pressure [KPa], work [J/ml], workrate [J/s·ml] are adopted as physical values.

The rendering apparatus according to the present embodiment sets a reference plane for the heart model 100. As an example, in FIGS. 1A and 1B, a plane that includes the fibrous ring of the mitral value located between the left atrium and the left ventricle is a reference plane S1. Further, the rendering apparatus sets in the reference plane S1, a rotational axis at a posterior aspect, posterior with respect to a viewpoint. The rendering apparatus sets multiple cross sections, respectively obtained by rotating the reference plane S1 about a rotational axis A by a given angle. The cross sections of the heart model 100 are a set of cross sections that pass through tetra elements forming the left ventricle of the heart model 100.

Hereinafter, a cross section of the heart model 100 is referred to as a "model cross section"; and a cross section of an element where a model cross section passes through a tetra element is referred to as an "element cross section". Physical values that tetra elements included in a model cross section have are assigned to the model cross section. The rendering apparatus performs a rendering process with respect to each model cross section, i.e., for each element cross section included in a model cross section, the rendering apparatus colors the model cross section according to the physical values that the element cross section has.

FIG. 1B depicts rendering of model cross sections C1 to C3 as viewed from the viewpoint. In the model cross sections C1 to C3, element cross sections are colored according to the physical values. Thus, by displaying the model cross sections C1 to C3, which are planes rotated a given amount from the reference plane S1 (planes forming given angles with the reference plane S1), variation of the physical value distribution from the anterior (with respect to a viewpoint P0) model cross section C1 to the posterior model cross section C3 becomes easy to see.

Figure 2:
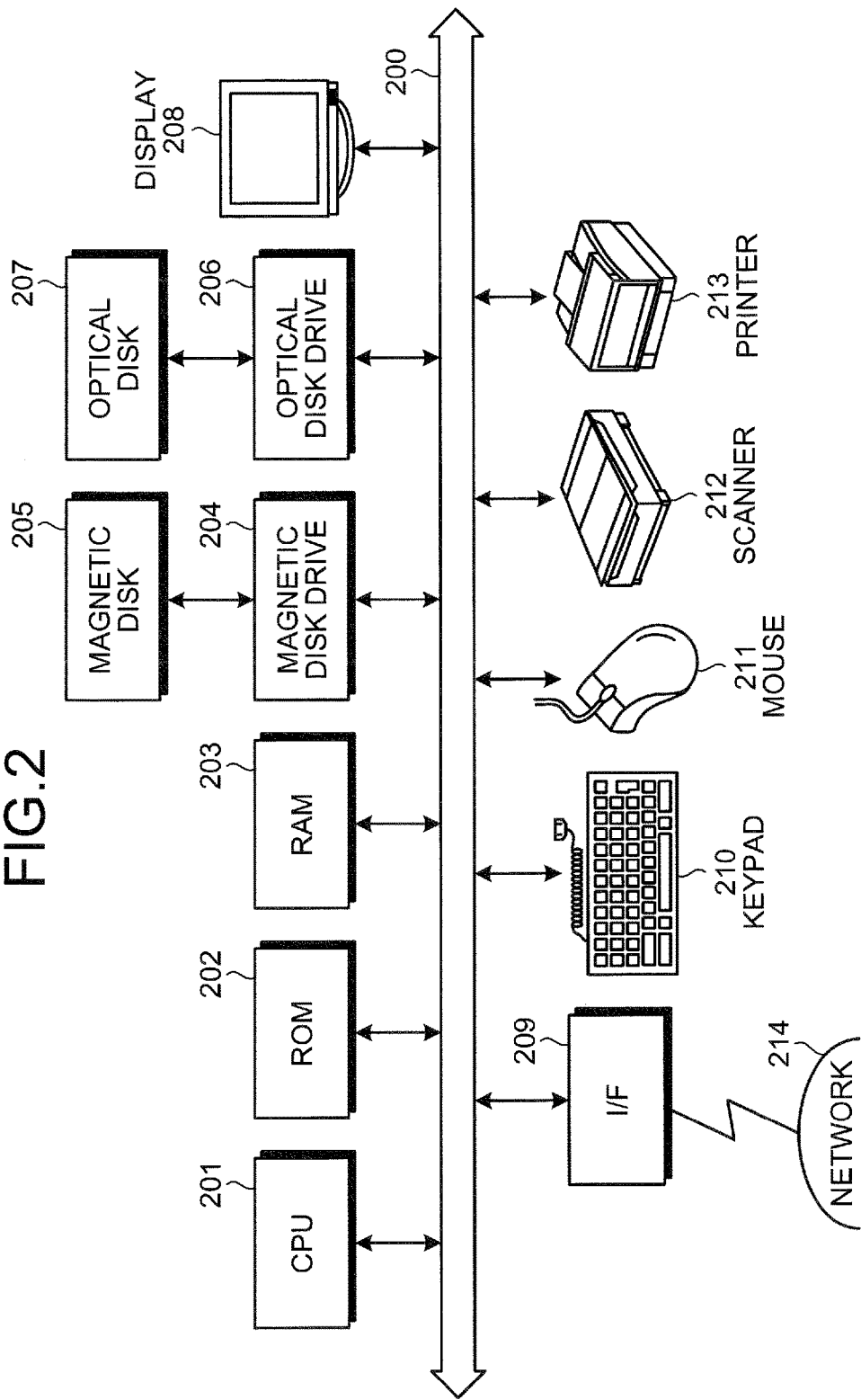
FIG. 2 is a block diagram of a hardware configuration of a rendering apparatus according to the first embodiment.

FIG. 2 is a block diagram of a hardware configuration of the rendering apparatus according to the first embodiment. As depicted in FIG. 2, the rendering apparatus includes a central processing unit (CPU) 201, read-only memory (ROM) 202, random access memory (RAM) 203, a magnetic disk drive 204, a magnetic disk 205, an optical disk drive 206, an optical disk 207, a display 208, an interface (I/F) 209, a keypad 210, a mouse 211, a scanner 212, and a printer 213, respectively connected by a bus 200.

The CPU 201 governs overall control of the rendering apparatus. The ROM 202 stores various types of programs such as a boot program. The RAM 203 is used as a work area of the CPU 201. The magnetic disk drive 204, under the control of the CPU 201, controls the reading and writing of data with respect to the magnetic disk 205. The magnetic disk 205 stores data written thereto under the control of the magnetic disk drive 204.

The optical disk drive 206, under the control of the CPU 201, controls the reading and writing of data with respect to the optical disk 207. The optical disk 207 stores data written thereto under the control of the optical disk drive 206, the data being read out from the optical disk 207 by a computer.

The display 208 is a display device that displays, for example, data such as text, images, functional information, etc., in addition to a cursor, icons, and/or tool boxes. A liquid crystal display, a plasma display, etc., may be employed as the display 508.

The I/F 209 is connected to a network 214 such as a local area network (LAN), a wide area network (WAN), and the Internet through a communication line and is connected to other apparatuses through the network 214. The I/F 209 administers an internal interface with the network 214 and controls the input/output of data from/to external apparatuses. For example, a modem or a LAN adaptor may be employed as the I/F 209.

The keypad 210 includes, for example, keys for inputting letters, numerals, and various instructions and performs the input of data. Alternatively, a touch-panel-type input pad or numeric keypad, etc. may be adopted. The mouse 211 is used to move the cursor, select a region, or move and change the size of windows. A track ball or a joy stick may be adopted provided each respectively has a function similar to a pointing device.

The scanner 212 optically reads an image into the rendering apparatus. The scanner 212 may have an optical character reader (OCR) function. The printer 213 prints image data and text data. The printer 213 may be, for example, a laser printer, an inkjet printer, and the like. Further, configuration may be such that at least any one among the optical disk drive 206, the optical disk 207, the display 208, the keypad 210, the mouse 211, the scanner 212, and the printer 213 is omitted.

Figure 3:
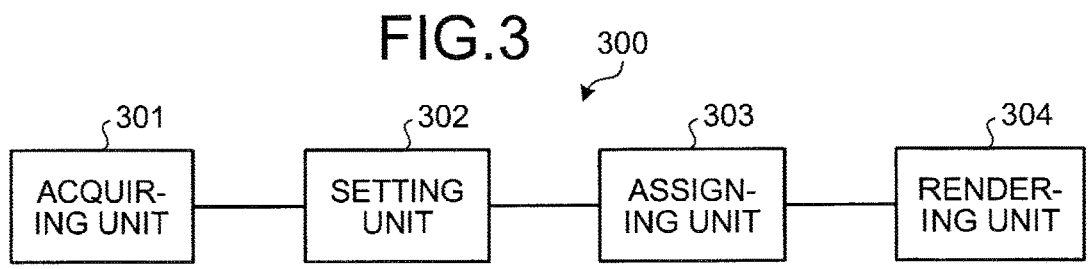
FIG. 3 is a block diagram of a functional configuration of the rendering apparatus according to the first embodiment.

FIG. 3 is a block diagram of a functional configuration of the rendering apparatus according to the first embodiment. A rendering apparatus 300 includes the acquiring unit 301, a setting unit 302, an assigning unit 303, and a rendering unit 304. Functions of the acquiring unit 301, the setting unit 302, the assigning unit 303, and the rendering unit 304 are, for example, implemented by executing on the CPU 301, a program stored in a storage device such as the RAM 203, the magnetic disk 205, and the optical disk 207 depicted in FIG. 2.

The acquiring unit 301 acquires an internal organ model that is a set of elements having physical values corresponding to positions of the internal organ. The internal organ model is a 3-dimensional model obtained through an analysis of behavior by simulation and is stored in a storage device. The acquiring unit 301, for example, from the storage device, reads out the heart model 100, as the internal organ model.

FIG. 4 is diagram depicting an example of a data structure of the heart model 100 according to the first embodiment. The heart model 100 is a data structure having for each tetra element, values of an ID field, a first vertex field to a fourth vertex field, a center of gravity field, a physical value field, an attribute field, and a cross section passing field.

The ID field stores a tetra element ID: i (where, i and a total tetra element count n are respectively integers satisfying $1 \leq i \leq n$). A tetra element ID is identifier information uniquely identifying a tetra element. A tetra element of the tetra element ID "i" is a tetra element ti. The first vertex field to the fourth vertex field respectively store vertex coordinate values of a first vertex $v1(ti)$ to a fourth vertex $v4(ti)$ for the tetra element ti. For the sake of convenience, the coordinate values will be indicated as $v1(ti)$ to $v4(ti)$. The first vertex $v1(ti)$ to the fourth vertex $v4(ti)$ are respectively the vertices of the tetra element ti, which is a tetrahedron.

The center of gravity field stores center of gravity coordinate values for the center of gravity $g(ti)$ of the tetra element ti. For the sake of convenience, the coordinate values will be indicated as $g(ti)$. The physical value field stores a physical value $e(ti)$ assigned to the tetra element ti. As described, a physical value is a value indicative of the behavior of the cardiac muscle corresponding to the tetra element; and, for example, pressure [KPa], work [J/ml], workrate [J/s·ml] are adopted as physical values.

The attribute field stores an attribute of the tetra element ti. The setting of an attribute is arbitrary. An attribute is information indicative of a property of the tetra element ti and, for example, is information indicating the site of the heart that the tetra element ti represents. For example, if the tetra element ti is positioned at the fibrous ring of the mitral valve, information indicating that the tetra element ti is a fibrous ring is stored in the attribute field of the tetra element ti. Therefore, if a plane that includes the fibrous ring is to be cut out, by referring to the attribute field, the rendering apparatus 300 can extract an element group that includes the tetra elements ti of the fibrous ring.

The cross section passing field stores a cross section passing flag. A cross section passing flag is an identifier indicating whether the model cross section passes through the tetra element ti. In the present example, a value of "1" for the cross section passing flag indicates that a model cross section passes through the tetra element ti and a value of "0" indicates that no model cross section passes through the tetra element ti. The cross section passing flag is information given by the setting unit 302.

FIG. 5 is a diagram depicting an example of tetra element ti according to the first embodiment. The shape of tetra element ti is a tetrahedron having the first vertex v1(ti) to the fourth vertex v4(ti). Further, at the center of gravity g(ti), a physical value e(ti) is assigned.

Reference of the description returns to FIG. 3. The setting unit 302 sets multiple planes that intersect the internal organ, forming given angles with the line of sight from the viewpoint P0. For example, the setting unit 302 sets multiple cross sections of the internal organ, forming an acute angle with the line of sight from the set viewpoint P0. For example, when a line segment that is in the reference plane S1 and orthogonal to the line of sight is regarded as the rotational axis A, by rotating the reference plane S1 by differing angles about the rotational axis A, multiple cross sections of the internal organ model, forming an acute angle with the line of sight are set. The position of the viewpoint P0 may be inside or outside the internal organ model.

For example, as depicted in FIGS. 1A and 1B, in the case of the heart model 100, the rendering apparatus 300 regards a plane that intersects the fibrous ring, to be the reference plane S1. The rendering apparatus 300, for example, regards a plane that intersects an element group extracted by referring to the attribute field of the heart model 100, to be the reference plane S1. Further, the reference plane S1 may be set by a user operation. In the case of setting by user operation, the rendering apparatus 300 can set the reference plane S1 by substituting into an equation of a plane, 3 points arbitrarily designated by the user and solving the equation.

The setting unit 302 uses the reference plane S1 and sets the rotational axis A. For example, the setting unit 302 sets a line segment that is orthogonal to the reference plane S1 and connects the viewpoint P0 and the reference plane S1, to be the line of sight from the viewpoint P0 toward the reference plane S1. Subsequently, the setting unit 302 sets multiple model cross sections that form acute angles with the line of sight. The viewpoint P0 may be set to be outside the internal organ model or may be set to be inside the internal organ model.

FIGS. 6A, 6B, and 6C are diagrams depicting an example of model cross section setting by the setting unit 302 according to the first embodiment. FIG. 6A depicts the reference plane S1 that includes a fibrous ring 600. FIG. 6B depicts line of sight setting. After setting the reference plane S1 as depicted in FIG. 6A, the rendering apparatus 300 sets a line segment that is from the viewpoint P0 toward the reference plane S1 and orthogonal to the reference plane S1, to be the line of sight. For example, since the state of cardiac muscle inside the heart is to be viewed, the setting unit 302 detects point P1, which in the reference plane S1 that includes the fibrous ring 600, is farthest from the viewpoint P0. The setting unit 302 detects a point P2 at a position that in a direction that is from the viewpoint P0 toward the reference plane S1 and orthogonal to the reference plane S1, is a given distance d0 from the detected point P1. The setting unit 302 sets a vector having the viewpoint P0 as a start point and the point P2 as an end point, to be a line of sight vector V. The direction indicated by the line of sight vector V is the line of sight. An angle $\alpha 0$ formed by the line of sight vector V and the reference plane S1 is an acute angle.

As depicted in FIG. 6C, the setting unit 302 further sets model cross sections at positions determined by rotating the reference plane S1 about the rotational axis A. The number of model cross sections and the rotation angle about the rotational axis A are, for example, set by the user. In the example depicted in FIG. 6C, 3 model cross sections and rotation angles of $\theta 1$ to $\theta 3$ are set. Further, angles $\alpha 1$ to $\alpha 3$ respectively formed by the model cross sections C1 to C3 and the line of sight vector V are set as acute angles. Thus, the model cross sections C1 to C3 are displayed in an easily viewable state as if viewed from the viewpoint P0. The setting unit 302 changes from "0" to "1", the cross section passing flag for a tetra element ti intersected by the model cross sections C1 to C3, whereby the tetra element ti intersected by a model cross section can be identified.

The reference of the description returns to FIG. 3. The assigning unit 303, among an element set, assigns physical values corresponding to elements intersected by the set planes, to element cross sections that are planes respectively intersecting the elements of the internal organ model. For example, the assigning unit 303, among an element set, assigns a physical value of a given element intersected by a model cross section, to a given element cross section obtained consequent to the model cross section of the internal organ model intersecting the given element. The assigning unit 303, for example, identifies from the data structure of the heart model 100 and from among a tetra element group forming the heart model 100, a tetra element intersected by the model cross sections C1 to C3, i.e., a tetra element ti whose cross section passing flag is "1". The assigning unit 303 detects an element cross section formed when the model cross sections C1 to C3 pass through the given tetra elements.

FIG. 7 is a diagram depicting a first example of element cross section detection according to the first embodiment. In FIG. 7, the assigning unit 303 detects an element cross section ckj where a given model cross section Ck (where, k is a model cross section number) intersects a tetra element ti. "j" is an element cross section number. The element cross section ckj is a triangle having a first vertex u1(ckj) to a third vertex u3(ckj). A physical value e(ti) of the search-source tetra element ti is assigned to the element cross section ckj FIG. 8 is diagram depicting a second example of element cross section detection according to the first embodiment. In FIG. 8, the assigning unit 303 detects an element cross section ckj where a given model cross section Ck intersects a tetra element ti. "j" is an element cross section number. In the example depicted in FIG. 8, the shape of the element cross section ckj is quadangular. In this case, the element cross section ckj is divided into 2 triangular element cross sections ckj1 and ckj2. The element cross section ckj1 is a triangle having a first vertex u11(ckj) to a third vertex u31(ckj). The element cross section ckj2 is a triangle having a first vertex u12(ckj) to a third vertex u32(ckj). A physical value e(ti) of the search-source tetra element ti is assigned to the element cross sections ckj1 and ckj2. Thus, by dividing the element cross section ckj, resolution of the model cross section improves.

The rendering unit 304 renders cross sections of multiple elements of an internal organ model 100 that has been assigned corresponding physical values, based on the physical values. For example, the rendering unit 304, with respect to a triangular polygon as a process unit, performs a rendering process of determining the normal of the triangular polygon and coloring. Thus, by making the element cross section into a triangular shape, an existing rendering process can be adopted.

FIG. 9 is a diagram depicting an example of the data structure of an element cross section according to the first embodiment. The element cross section is a data structure having for each element cross section, values for an ID field, a first vertex field to a third vertex field, and a physical value field.

The ID field stores an element cross section ID: j (where, j and a total element cross section count mk within a model cross section Ck described hereinafter are respectively integers satisfying 1≤j≤mk). "k" is a number identifying the model cross section Ck having an element cross section. "mk" is a total count of element cross sections within the model cross section Ck. The ID is identifier information uniquely identifying an element cross section. An ID within the model cross section Ck: an element cross section of the ID "j" is element cross section ckj. The first vertex field to the third vertex field store coordinate values of the first vertex u1(ckj) to the third vertex u3(ckj) of the element cross section ckj. For the sake of convenience, the coordinate values will be indicated as u1(ckj) to u3(ckj). The first vertex u1(ckj) to the third vertex u3(ckj) are respectively vertices of the element cross section ckj, which is a triangle. The physical value field stores a physical value e(ckj) that corresponds to the element cross section ckj. For example, a physical value e(ti) assigned to the tetra element ti detected by the element cross section ckj is stored as the physical value e(ckj).

The rendering unit 304, based on the physical values of given elements, renders cross sections of the internal organ model in which the physical values of the given elements are assigned to the cross sections of the given element. For example, the rendering unit 304, using the physical value assigned to the element cross section ckj, performs rendering on the model cross section Ck, which has the element cross section ckj. For example, the rendering unit 304 refers to a color map stored in a storage device and executes rendering.

FIG. 10 is diagram depicting an example of a color map according to the first embodiment. In the color map, for each physical value, values of the 3 primary colors, R (red), G (green), and B (blue), are set. A physical value of the color map may be an actual physical value or may be a normalized value of the actual physical value. For example, in the case of pressure, since a range of 0 to 200 [kPa] is set, a color map physical value range of 0 to 10 is associated and normalization is performed; and similarly in the case of work (e.g., −0.18 to 0.09[J/ml]) and workrate (e.g., −10 to 110[J·S·ml]. The rendering unit 304 refers to the color map, extracts for each element cross section ckj, the RGB values thereof, and executes rendering. Thus, a model cross section as depicted in FIG. 1B is displayed.

FIG. 11 is a flowchart of an example of a rendering process according to the first embodiment. The rendering apparatus 300, via the acquiring unit 301, acquires an internal organ model such as the heart model 100 (step S1101); and via the setting unit 302, sets model cross sections (step S1102). The rendering apparatus 300 determines whether an unselected model cross section is present (step S1103). If an unselected model cross section is present (step S1103: YES), the rendering apparatus 300 selects one of the unselected model cross sections (step S1104). The rendering apparatus 300 determines whether an unselected tetra element ti intersected by the selected model cross section is present (step S1105). If an unselected tetra element ti is present (step S1105: YES), the rendering apparatus 300 selects one of the unselected tetra elements ti (step S1106).

The rendering apparatus 300 detects an element cross section of the selected tetra element ti (step S1107). The rendering apparatus 300 determines whether the shape of the element cross section is triangular (step S1108). If the shape is triangular (step S1108: YES), the rendering apparatus 300 transitions to step S1110. On the other hand, if the shape is not triangular (step S1108: NO), the rendering apparatus 300 divides the quadangular element cross section into 2 triangles (step S1109), and transitions to step S1110. Thus, when a triangular element cross section is detected, the data structure of the element cross section is built as depicted in FIG. 9.

At step S1110, the rendering apparatus 300, via the assigning unit 303, assigns to the triangular element cross sections, the physical value of the selected tetra element ti (step S1110). For example, in the data structure of the element cross section, the rendering apparatus 300 stores the physical value of the selected tetra element ti into the record of the detected element cross section, and thereafter, returns to step S1105.

At step S1105, if no unselected tetra element ti that is intersected by the selected model cross section is present (step S1105: NO), the rendering apparatus 300 returns to step S1103. At step S1103, if no unselected model cross section is present (step S1103: NO), the physical values have been assigned to each of the element cross sections forming each model cross section. Consequently, the rendering apparatus 300, via the rendering unit 304, executes a rendering process (step S1111). Thus, each model cross section from the viewpoint P0 is displayed as depicted in FIG. 1B.

A second embodiment will be described. In the first embodiment, by rotating the reference plane S1 about the rotational axis A, multiple model cross sections are set. In the second embodiment, multiple model cross sections that are parallel to one another are set. For example, in the case of the heart model 100, the continuity of the physical values of the model cross sections become easy to view. Components and processes other than the model cross section setting are identical to those of the first embodiment and description thereof is omitted hereinafter.

FIGS. 12A and 12B are diagrams depicting a cross-section rendering example of the heart model 100. FIG. 12A depicts the heart model 100. The rendering apparatus 300 sets a reference plane S2 for the heart model 100. In FIGS. 12A and 12B, as an example, a cross section that intersects the heart model 100 longitudinally is the reference plane S2. The reference plane S2 is a cross section intersecting an apex 1200. The model cross sections C1 to C3 are set based on the reference plane S2. A setting method is described hereinafter.

FIG. 12B depicts the model cross sections C1 to C3 drawn as viewed from the viewpoint P0. In the model cross sections C1 to C3, the element cross sections have been colored according to the physical values. Thus, by displaying the model cross sections C1 to C3 along the rotating direction of the reference plane S2, the continuity of the physical values of the model cross sections C1 to C3 can be viewed easily.

FIG. 13 is diagram depicting an example of a setting method for the reference plane S1. In FIG. 13, reference numeral 1301 represents the mitral valve; and reference numeral 1302 represents the aortic value. When the mitral valve 1301, the aortic value 1302, and the apex 1200 are set respectively as attributes of a tetra element ti, setting can be performed automatically by the setting unit 302. Further, the setting unit 302 may be configured such that consequent to a user operation, data representing the mitral valve 1301, the aortic valve 1302, and the apex 1200 is set.

Reference numeral 1310 represents the center of gravity of the mitral valve 1301; and reference numeral 1320 represents the center of gravity of the aortic valve 1302. The center of gravity 1310 of the mitral valve 1301 may be calculated by the setting unit 302, using the coordinate values of the tetra element group forming the mitral valve 1301, or may be set by a user operation; and similarly for the center of gravity 1320 of the aortic valve 1302. Reference numeral 1330 is the midpoint of a line L1 connecting the center of gravity 1310 of the mitral valve 1301 and the center of gravity 1320 of the aortic valve 1302. The midpoint 1330 is calculated by the setting unit 302, using the center of gravity 1310 of the mitral valve 1301 and the center of gravity 1320 of aortic valve 1302. A plane that passes through the apex 1200 and the midpoint 1330, and is orthogonal to the line L1 is the reference plane S2. Further, a line L0 that passes through the apex 1200 and the midpoint 1330 is an axis, i.e., corresponds to the direction of blood flow of the heart.

FIG. 14 is diagram depicting an example of a setting method for a model cross section. In FIG. 14, 3 model cross sections are assumed. At the rendering apparatus 300, 2 angles θ and φ determining the orientation of the model cross sections C1 to C3 are set by the setting unit 302. The angle θ is an angle formed by a first line within the model cross sections C1 to C3 and a line within the reference plane S1, and as an example, is assumed to be a right angle. The first line is the line L1 passing through the center of gravity 1310 of the mitral valve 1301 and the center of gravity 1320 of the aortic valve 1302.

The line within the reference plane S2 is the line L0 passing through the apex 1200 and the midpoint 1330. The angle φ is an angle formed by the line L0 within the reference plane S2 and a second line (line L2) within the model cross sections C1 to C3. The line L2 is orthogonal to the line L1, and passes through an intersection of the line L1 and the line L0 that is within the reference plane S2. The angles θ and φ can be set by a user operation. The angles θ and φ are values common among the model cross sections C1 to C3 and therefore, the model cross sections C1 to C3 are parallel. Furthermore, the intervals between adjacent model cross sections are equivalent. The intervals between model cross sections can also be set by a user operation.

The model cross sections C1 to C3 form acute angles with the line of sight, by adjustment of the angle φ. For example, in a state where the viewpoint P0 and the line of sight have been determined, the angle φ is set such that the angle αformed by the line of sight and the model cross sections C1 to C3 becomes acute. In this manner, by setting the model cross sections C1 to C3, model cross sections can be displayed as depicted in FIG. 12B.

Thus, according to the first and the second embodiments, the viewability of continuous physical value distribution with respect to the internal organ can be improved. Further, by setting multiple model cross sections passing through the internal organ and displaying physical values on the model cross sections, distribution of the model cross section overall becomes easy to grasp for the user. Further, by setting the model cross section according to the structure of the internal organ, more efficient observation becomes possible.

For example, in the heart, the direction of blood flow is a direction from the mitral valve toward the apex during the diastolic phase and is a direction from the apex toward the aortic valve during the systolic phase. Therefore, by setting model cross sections at right angles to the direction of blood flow, model cross sections can be laid out as if the anterior side of the body has been opened. For example, when viewing is to be from a line of sight from the anterior side, the angles formed by the line of sight and the model cross sections are acute and the distribution of the model cross sections overall can be displayed in an easily viewable state.

Further, when the shape of an element cross section is quadrangular, by dividing the element cross section into 2 parts, resolution of the model cross section can be improved. By setting the element cross section to be a triangular shape, an existing rendering process can be adopted. Consequently, without altering the rendering process, the rendering process can be executed efficiently.

As described, the rendering program, the rendering method, and the rendering apparatus enable improved viewability of continuous physical value distribution with respect to an internal organ.

All examples and conditional language provided herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable recording medium storing a rendering program that causes a computer to execute a process comprising:
   acquiring an internal organ model that is a set of tetrahedral elements having physical values according to each position of an internal organ;
   setting a plurality of planes that form given angles with a line of sight from a viewpoint position, and intersect the internal organ model;
   assigning, among the set of tetrahedral elements, a value of pressure, work, or workrate indicative of a behavior of a cardiac muscle corresponding to an element of a tetrahedral element intersected by a plane set at the setting to a tetrahedral element cross section that is a plane where the plane set at the setting intersects the tetrahedral element; and
   coloring, according to the value of pressure, work, or workrate indicative of the behavior of the cardiac muscle, the tetrahedral element cross section to which the value has been assigned, wherein
   the setting includes setting as a rotational axis a line that is orthogonal to the line of sight and is in a reference plane that intersects the internal organ model and forms a given angle with the line of sight and rotating the reference plane by varying rotation angles about the rotational axis to set the planes that form the given angles with the line of sight,
   the internal organ model is an internal organ model of a heart, and
   the setting includes setting as the reference plane, a plane that passes through a fibrous ring of the heart, and setting the planes that form the given angles with the line of sight.

2. The non-transitory computer-readable recording medium according to claim 1, wherein
   the setting includes setting the planes to be orthogonal to a reference plane intersecting the internal organ model and to form the given angles with the line of sight.

3. The non-transitory computer-readable recording medium according to claim 2, wherein the internal organ model is an internal organ model of a heart, and the setting includes setting as a reference plane, a plane that includes a line representing a blood flow direction of the heart, and setting the planes that form the given angles with the line of sight.

4. The non-transitory computer-readable recording medium according to claim 1, the process further comprising dividing into two triangles, the tetrahedral element cross section, when the tetrahedral element cross section is of a quadrangular shape, wherein the assigning includes assigning to each of the triangles, the value of the tetrahedral element cross section.

5. A rendering method executed by a computer comprising a processor and a storage device, the rendering method comprising:

acquiring, by the processor from the storage device, an internal organ model that is a set of tetrahedral elements having physical values according to each position of an internal organ;

setting, by the processor, a plurality of planes that form given angles with a line of sight from a viewpoint position, and intersect the internal organ model;

assigning, by the processor, among the set of tetrahedral elements, a value of pressure, work, or workrate indicative of a behavior of a cardiac muscle corresponding to an element of a tetrahedral element intersected by a plane set at the setting to a tetrahedral element cross section that is a plane where the plane set at the setting intersects the tetrahedral element; and coloring, by the processor, according to the value of pressure, work, or workrate indicative of the behavior of the cardiac muscle, the tetrahedral element cross section to which the physical value has been assigned, wherein the setting includes setting as a rotational axis, a line that is orthogonal to the line of sight and is in a reference plane that intersects the internal organ model and forms a given angle with the line of sight and rotating the reference plane by varying rotation angles about the rotational axis to set the planes that form the given angles with the line of sight, the internal organ model is an internal organ model of a heart, and the setting includes setting as the reference plane, a plane that passes through a fibrous ring of the heart, and setting the planes that form the given angles with the line of sight.

6. A rendering apparatus comprising:

a processor; and a memory which stores a plurality of instructions, which when executed by the processor, cause the processor to execute:

acquiring an internal organ model that is a set of tetrahedral elements having physical values according to each position of an internal organ;

setting a plurality of planes that form given angles with a line of sight from a viewpoint position, and intersecting the internal organ model;

assigning, among the set of tetrahedral elements, a value of pressure, work, or workrate indicative of a behavior of a cardiac muscle corresponding to an element of a tetrahedral element intersected by a plane set at the setting to a tetrahedral element cross section that is a plane where the plane set at the setting intersects the tetrahedral element; and coloring, according to the value of pressure, work, or workrate indicative of the behavior of the cardiac muscle, the tetrahedral element cross section to which the physical value has been assigned, wherein the setting includes setting as a rotational axis, a line that is orthogonal to the line of sight and is in a reference plane that intersects the internal organ model and forms a given angle with the line of sight and rotating the reference plane by varying rotation angles about the rotational axis to set the planes that form the given angles with the line of sight, the internal organ model is an internal organ model of a heart, and the setting includes setting as the reference plane, a plane that passes through a fibrous ring of the heart, and setting the planes that form the given angles with the line of sight.

* * * * *